(12) United States Patent
Bendall

(10) Patent No.: US 11,900,590 B2
(45) Date of Patent: Feb. 13, 2024

(54) INSPECTION DEVICE ARTICULATION TRANSFORMATION BASED ON IMAGE TRANSFORMATION

(71) Applicant: Baker Hughes Holdings LLC, Houston, TX (US)

(72) Inventor: Clark A. Bendall, Skaneateles, NY (US)

(73) Assignee: Baker Hughes Holdings LLC, Houston, TX (US)

( * ) Notice: Subject to any disclaimer, the term of this patent is extended or adjusted under 35 U.S.C. 154(b) by 114 days.

(21) Appl. No.: 17/501,711

(22) Filed: Oct. 14, 2021

(65) Prior Publication Data

US 2022/0122242 A1     Apr. 21, 2022

Related U.S. Application Data

(60) Provisional application No. 63/094,397, filed on Oct. 21, 2020.

(51) Int. Cl.
*G06T 7/00* (2017.01)
*G01N 21/954* (2006.01)
(Continued)

(52) U.S. Cl.
CPC ......... *G06T 7/001* (2013.01); *G01N 21/8803* (2013.01); *G01N 21/954* (2013.01); *G02B 23/2484* (2013.01); *G01N 2021/8861* (2013.01)

(58) Field of Classification Search
CPC ......... A61B 34/76; A61B 34/30; A61B 34/35; A61B 34/37; A61B 34/70;
(Continued)

(56) References Cited

U.S. PATENT DOCUMENTS 8,864,655 B2 * 10/2014 Ramamurthy ....... A61B 5/0059
600/117
9,504,484 B2 * 11/2016 Andrews ................ A61B 34/20
(Continued)

OTHER PUBLICATIONS

International Search Report and Written Opinion received for PCT International Application No. PCT/US2021/071947, dated Feb. 16, 2022, 10 pgs.

*Primary Examiner* — Isiaka O Akanbi
(74) *Attorney, Agent, or Firm* — Mintz Levin Cohn Ferris Glovsky and Popeo, P.C.

(57) ABSTRACT

A method can include receiving image data characterizing a viewed object acquired via an image sensor of a visual inspection system and providing the image data in a display. The method can include receiving a first directional movement input via a directional input device of the visual inspection system and applying a first set of actuator drive signals to a plurality of actuators of the visual inspection system. The method can further include applying a coordinate transformation to the image data to generate transformed image data and receiving a second directional movement input via the directional input device. The method can also include applying a second set of actuator drive signals to the plurality of actuators. The second set of actuator drive signals can cause points on the viewed object to move in the first direction on the display. Related systems performing the method are also provided.

14 Claims, 4 Drawing Sheets

(51) Int. Cl.
*G01N 21/88* (2006.01)
*G02B 23/24* (2006.01)

(58) Field of Classification Search
CPC .... A61B 17/00234; A61B 90/361; B25J 3/04; B25J 9/1689; B25J 19/023; G06T 1/0014; G06T 3/00; H04N 13/239; H04N 13/246; H04N 13/296; H04N 13/337; H04N 13/341; H04N 13/398; H04N 13/189; H04N 13/194; G03C 1/0053; G05B 2219/35506; G05B 2219/39389; G05B 2219/40158; G05B 2219/40161; G05B 2219/40169; G05B 2219/45123
USPC ........ 356/137, 614–624, 364; 382/138, 141; 600/130, 117–118

See application file for complete search history.

(56) References Cited

U.S. PATENT DOCUMENTS

| | | | |
|---|---|---|---|
| 2001/0046313 A1 | 11/2001 | Green | |
| 2003/0114730 A1 | 6/2003 | Hale et al. | |
| 2005/0054895 A1* | 3/2005 | Hoeg | A61B 90/36 600/117 |
| 2008/0152210 A1* | 6/2008 | Bendall | H04N 23/81 382/141 |
| 2015/0053025 A1* | 2/2015 | Coombs | G01N 21/84 73/866.5 |
| 2019/0083187 A1* | 3/2019 | Danitz | A61B 34/32 |
| 2019/0380566 A1* | 12/2019 | Charles | A61B 17/1628 |
| 2020/0078103 A1* | 3/2020 | Duindam | A61B 1/00097 |
| 2020/0405403 A1* | 12/2020 | Shelton, IV | A61B 46/10 |
| 2021/0369366 A1* | 12/2021 | Hwang | A61B 34/74 |

* cited by examiner

INSPECTION DEVICE ARTICULATION TRANSFORMATION BASED ON IMAGE TRANSFORMATION

RELATED APPLICATION

This application claims priority under 35 U.S.C. § 119(e) to U.S. Provisional Application No. 63/094,397, filed Oct. 21, 2020, the entire contents of which are hereby expressly incorporated by reference herein.

TECHNICAL FIELD

The subject matter herein relates to automated visual inspection of industrial equipment.

BACKGROUND

Visual inspection tools can include a articulating camera configured to provide a view of industrial equipment being inspected. The camera can be configured on an inspection device, such as a video borescope. The camera can be maneuvered into position to capture inspection data by steering commands supplied by a user. The steering commands can be provided as inputs to a camera control of the inspection device, such as a joystick. The inspection device can include a display configured to display visual inspection data in relation to the steering commands. When the displayed image is digitally rotated, the intuitive correspondence between a steering command and an expected image portion to be displayed can be lost.

SUMMARY

During visual inspection of industrial equipment, an inspection image can be rotated by a user. The user can rotate the inspection image using software menu options, physical interaction mechanisms or buttons, or interactive gestures supplied to a display of the inspection device. Upon rotating the inspection image, the display may no longer provide the intuitive correspondence between steering commands and displayed image portions. Compensation can be applied to inspection image data to maintain a consistent, intuitive correspondence between steering commands and the resulting image translation in the display of the inspection data.

In one aspect, a method is provided. In an embodiment, the method can include receiving image data characterizing a viewed object. The image data can be acquired via an image sensor of a visual inspection system. The method can also include providing the image data via a display of the visual inspection system. The method can further include receiving a first directional movement input via a directional input device of the visual inspection system. The method can also include applying a first set of actuator drive signals to a plurality of actuators of the visual inspection system to move the image sensor. The first set of actuator drive signals can cause points on the viewed object to move in a first direction on the display. The method can further include applying a coordinate transformation to the image data to generate transformed image data. The method can also include displaying the transformed image data on the display. The method can further include receiving a second directional movement input via the directional input device. The second directional movement input can be the same as the first directional movement input. The method can also include applying a second set of actuator drive signals to the plurality of actuators of the visual inspection system to move the image sensor. The second set of actuator drive signals causing points on the viewed object to move in the first direction on the display.

One or more variations of the subject matter herein are feasible. For example, in another embodiment, the coordinate transformation can include at least one of a horizontal mirroring transformation, a vertical mirroring transformation, or a rotation transformation. The visual inspection system can be a video borescope. The image data and the transformed image data can be provided for display during an inspection of industrial equipment using the visual inspection system. The coordinate transformation can be applied via a manual gesture provided via the display or via a menu selection provided via the display.

The method can also include providing a tip map graphic in the display. The tip map graphic can include an indicator. A position of the indicator within the tip map graphic can correspond to a direction and an amount of movement of the plurality of actuators. The indicator can move in the same direction in response to the first directional movement input and the second directional movement input. The plurality of actuators can be articulated via pneumatic, hydraulic, memory metal, or direct drive articulation mechanisms.

In another aspect, a borescope system is provided. In an embodiment, the borescope system can include an image sensor, a display, a plurality of actuators mechanically coupled to the image sensor, a directional input device, a processor, and a memory storing computer-readable executable instructions. The plurality of actuators can move the image sensor based on received actuator drive signals and the processor can be configured to execute the instructions to cause the processor to perform operations. The operations can include receiving image data characterizing a viewed object acquired via the image sensor. The operations can also include providing the image data via the display. The operations can further include receiving a first directional movement input via the directional input device. The operations can also include applying a first set of actuator drive signals to the plurality of actuators to move the image sensor. The first set of actuator drive signals can cause points on the viewed object to move in a first direction on the display. The operations can further include applying a coordinate transformation to the image data to generate transformed image data. The operations can also include displaying the transformed image data on the display. The operations can further include receiving a second directional movement input via the directional input device. The second directional movement input can be the same as the first directional movement input. The operations can also include applying a second set of actuator drive signals to the plurality of actuators to move the image sensor. The second set of actuator drive signals causing points on the viewed object to move in the first direction on the display.

Non-transitory computer program products (i.e., physically embodied computer program products) are also described herein that store instructions, which when executed by one or more data processors of one or more computing systems, causes at least one data processor to perform operations herein. Similarly, computing devices and systems are also described herein that may include one or more data processors and memory coupled to the one or more data processors. The memory may temporarily or permanently store instructions that cause at least one processor to perform one or more of the operations described herein. In addition, methods can be implemented by one or more data processors either within a single computing system or distributed among two or more computing systems. Such computing systems can be connected and can exchange data and/or commands or other instructions or the like via one or more connections, including a connection over a network (e.g. the Internet, a wireless wide area network, a local area network, a wide area network, a wired network, or the like), via a direct connection between one or more of the multiple computing systems, etc.

DESCRIPTION OF DRAWINGS

These and other features will be more readily understood from the following detailed description taken in conjunction with the accompanying drawings, in which.

Figure 1:
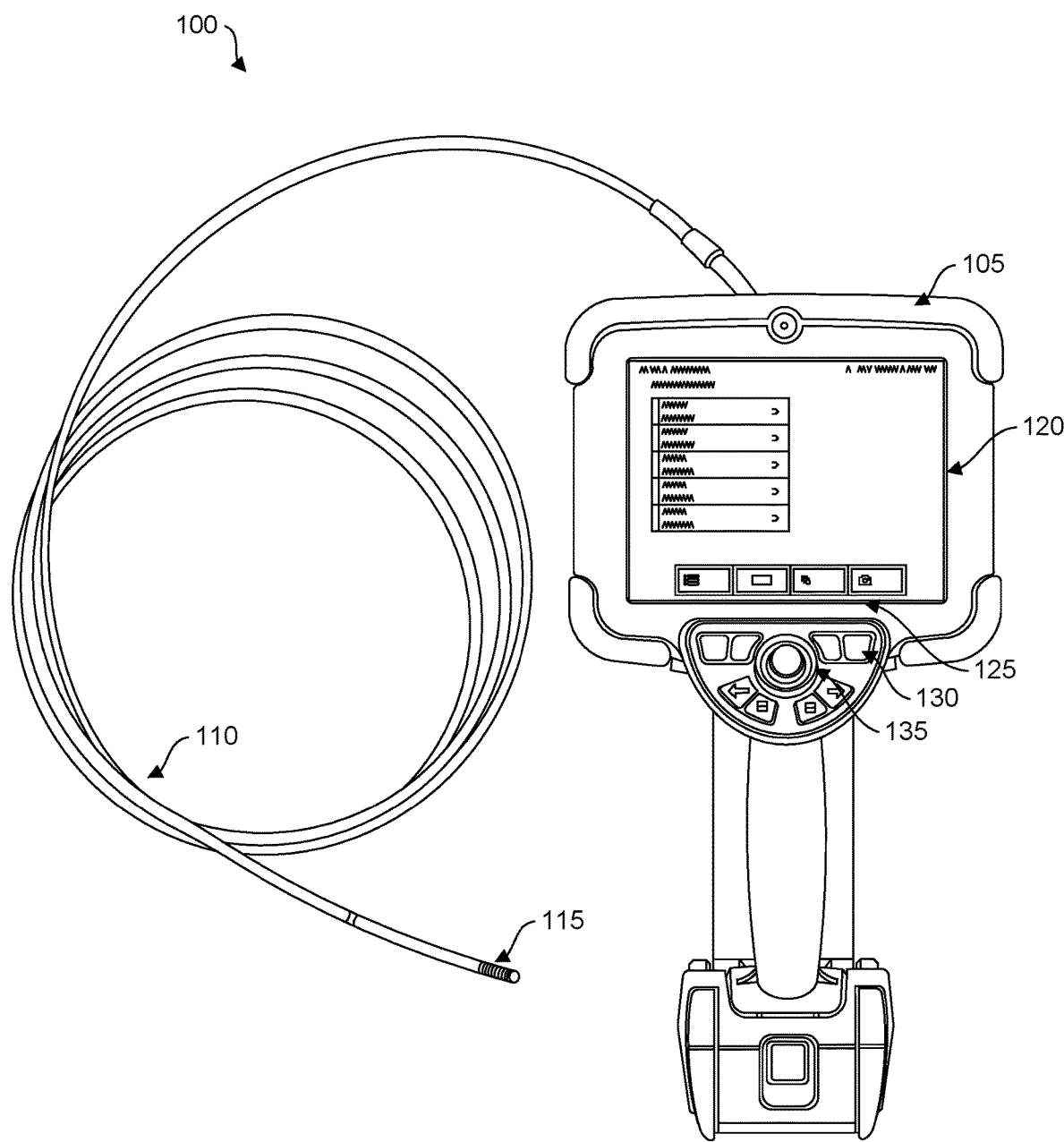
FIG. 1 is a diagram illustrating an example of a visual inspection device according to embodiments described herein.

It is noted that the drawings are not necessarily to scale. The drawings are intended to depict only typical aspects of the subject matter disclosed herein, and therefore should not be considered as limiting the scope of the disclosure.

DETAILED DESCRIPTION

Embodiments of the present disclosure describe systems, apparatuses, methods, and computer-readable mediums for determining and providing image transformations for rotated inspection data for use in visual inspection and monitoring of industrial equipment in an oil and gas production environment. However, it can be understood that embodiments of the disclosure can be employed for determining and providing image transformations for rotated inspection data for industrial equipment in any environment or in non-industrial environments without limit.

In visual inspection devices, such as video borescopes, a camera can be steered to view an object being inspected using motor-driven articulation. The camera can be articulated by two pairs of articulation cables that connect a flexible tip housing the camera to two motors. One more can control movement in a left/right or X-axis direction. The second motor can control movement in an up/down or Y-axis direction. The cables can be rigidly attached to a distal end of the flexible tip. The camera (or an image sensor) can be configured within the flexible tip to acquire and produce image data for displaying an inspection image on a display of the visual inspection device.

The visual inspection device can also include a joystick or a touch-screen display as input devices. The user can provide steering commands to maneuver the flexible tip and the camera in response to the steering commands. For example, a user may push a joystick to the left when the user seeks to display a portion of the object being inspected that is outside the current field of view of the camera and is to the left of the current field of view. The joystick movement can be translated into a motor command that can cause a first motor associated with movement in the X-axis direction to pull on a cable and to cause the flexible tip to bend to the left. As a result, the desired portion of the object being inspected can be brought into view on the display. Similarly, the user can push the joystick up, down, or right, to induce motor movements that pull on the particular cables associated with the up, down, or right desired steering motions applied to the joystick by the user. Thus, an intuitive relationship is provided by the visual inspection device between the movement of the joystick, the movement of the flexible tip and camera, and the resultant inspection image provided in the display.

When the displayed image is digitally rotated, however, the steering can become non-intuitive because a upward push of the joystick no longer results in a corresponding image translation in that same upward direction. This can make it difficult to control steering the visual inspection device to bring desired portions of the object being inspected into view within the display. A user can rotate the inspection image by applying a two-finger touch gesture to a touch-screen display of the visual inspection device. A two-finger gesture can be used to input continuous rotation control. In some embodiments, a user can also rotate the inspection image by selecting one or more menu options provided on a graphical user interface provided in a display of the visual inspection device. The menu options can be executed to sequentially perform the image rotation in 90 degree increments.

In response to the image being rotated, the subject matter described herein can apply a compensation transformation in the process of determining the motor commands responsive to joystick movement such that the expected, intuitive correspondence between joystick motion and image translation is maintained. For example, when the joystick (or other input device) outputs an X value ranging from −1 (e.g., when the joystick is pushed fully to the left) to +1 (e.g., when the joystick is pushed fully to the right), the transformed X values can be computed as shown in equation 1.

$$x'=x*\cos(theta)-y*\sin(theta) \tag{1}$$

Similarly, when the joystick (or other input device) outputs a Y value ranging from −1 (e.g., when the joystick is pushed fully down) to +1 (e.g., when the joystick is pushed fully up), the transformed Y values can be computed as shown in equation 2.

$$y'=y*\sin(theta)+y*\cos(theta) \tag{2}$$

In some embodiments, other transforms such as horizontal mirroring of video and steering can applied. For example, a horizontal mirroring transform can be applied such that $x'=-x$. In some embodiments, the other transforms to be applied can include vertical mirroring of video and steering. For example, a vertical mirroring transform can be applied such that $y'=-y$.

In some embodiments, the visual inspection device, or an inspection system coupled to the visual inspection device can display a graphical indicator of steering commands being provided to the motors associated with X-axis movement and Y-axis movement. For example, a square can be displayed with a dot showing where the steering command falls within possible X and Y-axis ranges. For non-rotated images, the dot would move left, right, up, or down when the joystick is moved left, right, up, or down. For rotated images, and when the compensation transforms described above in equations 1 and 2 are applied, the dot movement may normally no longer follow the joystick directions. In one embodiment, a second compensation transformation can be applied to the position values used to set the position of the dot in the displayed tip map graphic. The second compensation transformation can be implemented as described in equations 3 and 4.

$$x''=x'*\cos(theta)+y'*\sin(theta) \tag{3}$$

$$y''=-x'*\sin(theta)+y'*\cos(theta) \tag{4}$$

Although the subject matter herein describes visual inspection tools using motors and cables for articulation, other embodiments can use pneumatic, hydraulic, memory metal, or direct driven articulation mechanisms or systems. In these systems, the coordinate transformations described herein can be applied while translating user-provided steering commands into mechanical system commands which are responsive to the steering commands and configured to adjust a position of an image sensor or camera of the visual inspection device.

FIG. 1 is a diagram 100 illustrating an example of a visual inspection device 105 according to embodiments described herein. In some embodiments, the visual inspection device 105 can include a video borescope. As shown in FIG. 1, the visual inspection device 105 can include an insertion tube 110 to be inserted into an object undergoing inspection. The insertion tube 110 can include a flexible tip 115 which can be articulated via the inspection device 105. The inspection device can also include a display 120 configured to provide a graphical user interface 125. The visual inspection device 105 can also include one or more buttons 130 and a joystick 135. The buttons 130 and/or the joystick 135 can be configured to receive user inputs and to generate signals indicative of steering commands associated with the user inputs.

Figure 2:
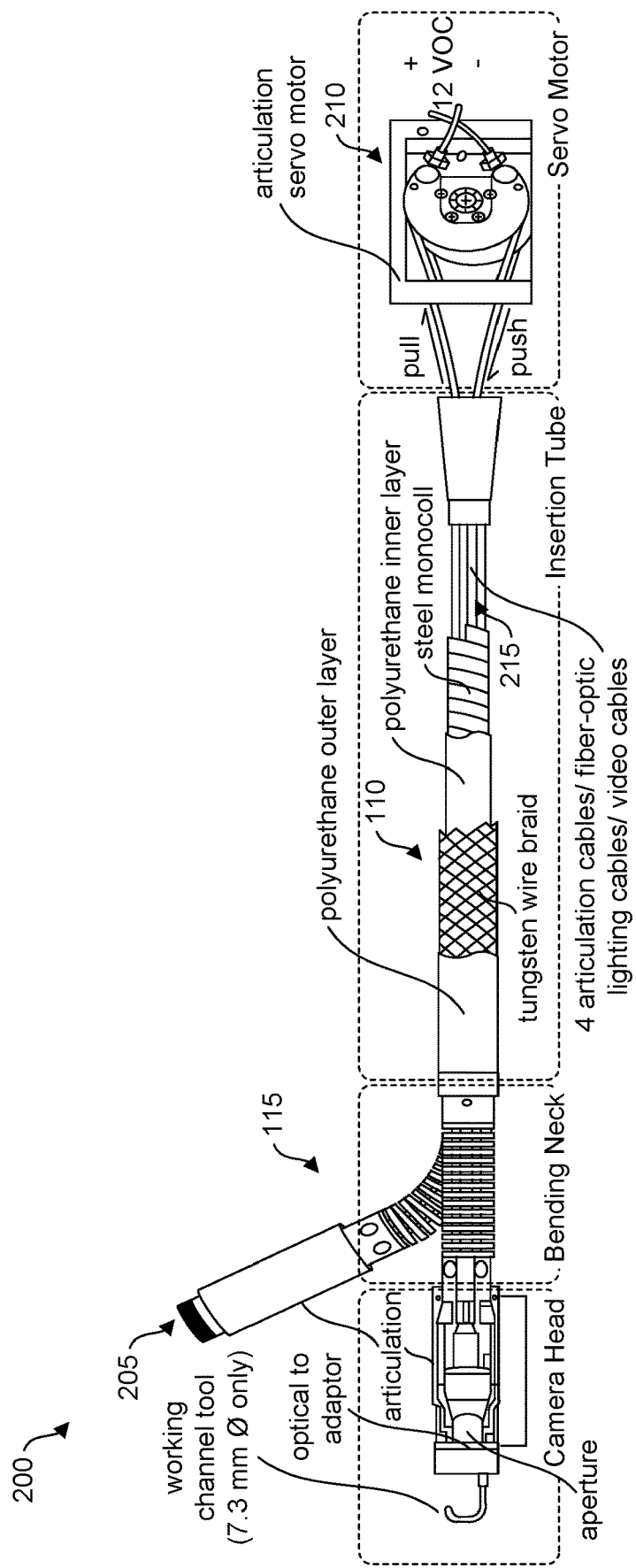
FIG. 2 is a diagram illustrating a portion of the visual inspection device of FIG. 1.

FIG. 2 is a diagram 200 illustrating a portion of the visual inspection device 105 of FIG. 1. As shown in FIG. 2, the flexible tip 115 can include a camera 205 configured to acquire visual inspection data. The flexible tip 115 can be mechanically coupled to two or more motors or actuators 210. The motors actuators 210 can be configured to receive the input signal indicative of a steering command and to actuate in response to the input signal. Cables 215 can couple the motors actuators 210 to the flexible tip 115 such that actuation of the motor 210 can cause the cables 215 to be pulled or loosened and can cause the flexible tip 115 to move in a direction associated with the steering command.

Figure 3:
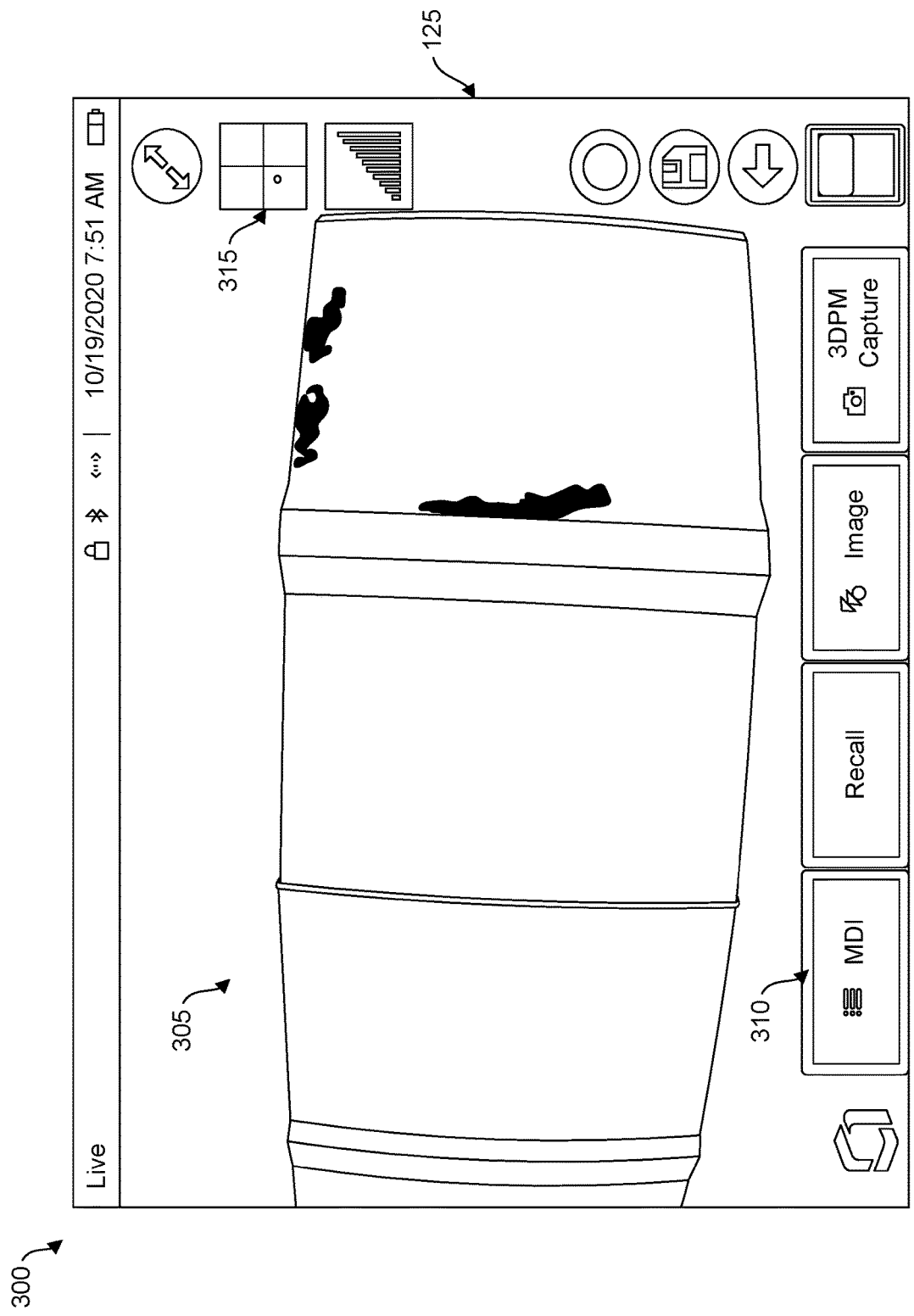
FIG. 3 is a diagram illustrating an example of a graphical user interface of the visual inspection device of FIG. 1 according to embodiments described herein.

FIG. 3 is a diagram 300 illustrating an example of a graphical user interface (GUI) 125 of the visual inspection device 105 of FIG. 1 according to embodiments described herein. As shown in FIG. 3, the GUI 125 can provide inspection image data 305 of an object being inspected. The GUI 125 can also include a menu 310. In some embodiments, the menu 310 can be configured for interactive touch inputs, such as when the display 120 of the visual inspection device 105 is a touch-screen display. The GUI 125 can also display a tip map graphic 315. The tip map graphic 315 can depict quadrants representing the range of articulation space along X and Y axes. The tip map graphic 315 can include an indicator, such as a dot, therein indicating the position of the most recent (or current) steering command input.

The subject matter described herein advantageously maintains intuitive correspondence between steering commands provided via a joystick, touch-screen interface, or software menu options and translation of a displayed image and tip map dot position when the displayed image is digitally rotated.

Figure 4:
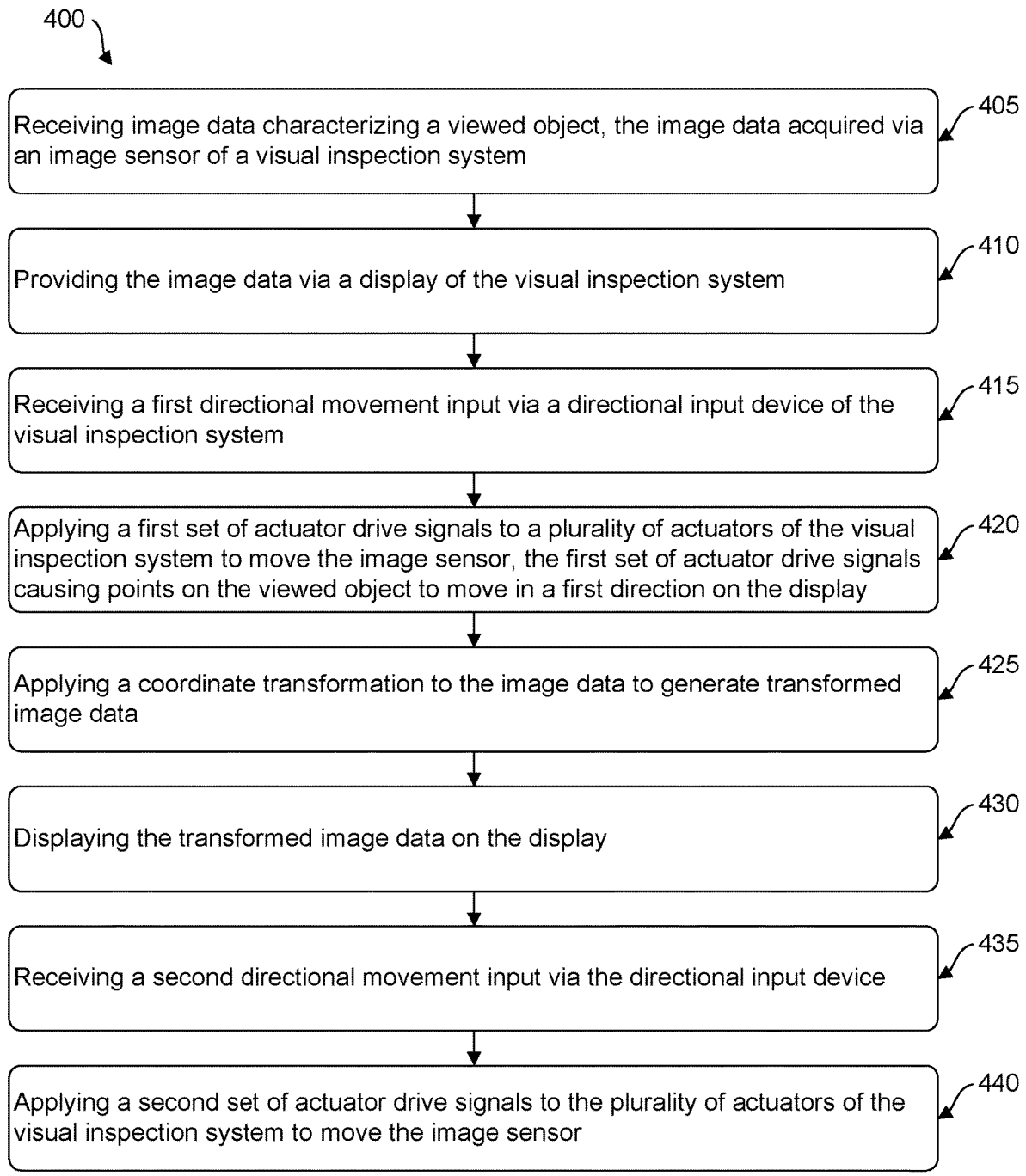
FIG. 4 is a flow diagram depicting a process for transforming image data based on inspection device articulation transformation.

FIG. 4 is a flow diagram depicting a process 400 for transforming image data based on inspection device articulation transformation. As shown in FIG. 4, at 405, a visual inspection system as described herein can receive image data characterizing a viewed object. In some embodiments, the visual inspection system can be a video borescope. The image data can be acquired via an image sensor of the visual inspection system. At 410, a processor of the visual inspection system can provide the image data via a display of the visual inspection system. At 415, a first directional movement input can be received via a directional input device of the visual inspection system. For example, the directional input device can include a joystick configured on the visual inspection system.

At 420, the processor of the visual inspection system can apply a first set of actuator drive signals to a plurality of actuators of the visual inspection system. The actuator drive signals can move the image sensor. The first set of actuator drive signals can cause points on the viewed object to move in a first direction on the display. In some embodiments, the plurality of actuators can be articulated via pneumatic, hydraulic, memory metal, or direct drive articulation mechanisms. At 425, the processor of the visual inspection system can apply a coordinate transformation to the image data to generate transformed image data. In some embodiments, the coordinate transformation includes at least one of a horizontal mirroring transformation, a vertical mirroring transformation, or a rotation transformation. In some embodiments, the coordinate transformation can be applied via a manual gesture provided via the display. In some embodiments, the coordinate transformation can be applied via a menu selection provided via the display. At 430, the processor can cause the transformed image data to be displayed on the display of the visual inspection system. In some embodiments, the image data and the transformed image data can be provided for display during an inspection of industrial equipment performed using the visual inspection system. In some embodiments, the industrial equipment can be configured in an oil and gas production environment, an aviation system, or can include rotating or turbomachinery equipment.

At 435, a second directional movement input can be received via the directional input device of the visual inspection system. The second directional movement input can be the same as the first directional movement input. At 440, the processor of the visual inspection system can apply a second set of actuator drive signals to the plurality of actuators of the visual inspection system to move the image sensor. The second set of actuator drive signals can cause points on the viewed object to move in the first direction on the display.

In some embodiments, the process 400 can further include providing a tip map graphic in the display. The tip map graphic can include an indicator. A position of the indicator within the tip map graphic can correspond to a direction and an amount of movement of the plurality of actuators. The indicator can move in the same direction in response to the first directional movement input and the second directional input movement.

Certain exemplary embodiments have been described to provide an overall understanding of the principles of the structure, function, manufacture, and use of the systems, devices, and methods disclosed herein. One or more examples of these embodiments have been illustrated in the accompanying drawings. Those skilled in the art will understand that the systems, devices, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention. Further, in the present disclosure, like-named components of the embodiments generally have similar features, and thus within a particular embodiment each feature of each like-named component is not necessarily fully elaborated upon.

The subject matter described herein can be implemented in analog electronic circuitry, digital electronic circuitry, and/or in computer software, firmware, or hardware, including the structural means disclosed in this specification and structural equivalents thereof, or in combinations of them. The subject matter described herein can be implemented as one or more computer program products, such as one or more computer programs tangibly embodied in an information carrier (e.g., in a machine-readable storage device), or embodied in a propagated signal, for execution by, or to control the operation of, data processing apparatus (e.g., a programmable processor, a computer, or multiple computers). A computer program (also known as a program, software, software application, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file. A program can be stored in a portion of a file that holds other programs or data, in a single file dedicated to the program in question, or in multiple coordinated files (e.g., files that store one or more modules, sub-programs, or portions of code). A computer program can be deployed to be executed on one computer or on multiple computers at one site or distributed across multiple sites and interconnected by a communication network.

The processes and logic flows described in this specification, including the method steps of the subject matter described herein, can be performed by one or more programmable processors executing one or more computer programs to perform functions of the subject matter described herein by operating on input data and generating output. The processes and logic flows can also be performed by, and apparatus of the subject matter described herein can be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processor of any kind of digital computer. Generally, a processor will receive instructions and data from a read-only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example semiconductor memory devices, (e.g., EPROM, EEPROM, and flash memory devices); magnetic disks, (e.g., internal hard disks or removable disks); magneto-optical disks; and optical disks (e.g., CD and DVD disks). The processor and the memory can be supplemented by, or incorporated in, special purpose logic circuitry.

To provide for interaction with a user, the subject matter described herein can be implemented on a computer having a display device, e.g., a touch-screen display, a cathode ray tube (CRT) or liquid crystal display (LCD) monitor, for receiving inputs and for displaying information to the user and a keyboard and a pointing device, (e.g., a mouse or a trackball), by which the user can provide input to the computer. Other kinds of devices can be used to provide for interaction with a user as well. For example, feedback provided to the user can be any form of sensory feedback, (e.g., visual feedback, auditory feedback, or tactile feedback), and input from the user can be received in any form, including acoustic, speech, or tactile input.

The techniques described herein can be implemented using one or more modules. As used herein, the term "module" refers to computing software, firmware, hardware, and/or various combinations thereof. At a minimum, however, modules are not to be interpreted as software that is not implemented on hardware, firmware, or recorded on a non-transitory processor readable recordable storage medium (i.e., modules are not software per se). Indeed "module" is to be interpreted to always include at least some physical, non-transitory hardware such as a part of a processor or computer. Two different modules can share the same physical hardware (e.g., two different modules can use the same processor and network interface). The modules described herein can be combined, integrated, separated, and/or duplicated to support various applications. Also, a function described herein as being performed at a particular module can be performed at one or more other modules and/or by one or more other devices instead of or in addition to the function performed at the particular module. Further, the modules can be implemented across multiple devices and/or other components local or remote to one another. Additionally, the modules can be moved from one device and added to another device, and/or can be included in both devices.

The subject matter described herein can be implemented in a computing system that includes a back-end component (e.g., a data server), a middleware component (e.g., an application server), or a front-end component (e.g., a client computer having a graphical user interface or a web browser through which a user can interact with an implementation of the subject matter described herein), or any combination of such back-end, middleware, and front-end components. The components of the system can be interconnected by any form or medium of digital data communication, e.g., a communication network. Examples of communication networks include a local area network ("LAN") and a wide area network ("WAN"), e.g., the Internet.

Approximating language, as used herein throughout the specification and claims, may be applied to modify any quantitative representation that could permissibly vary without resulting in a change in the basic function to which it is related. Accordingly, a value modified by a term or terms, such as "about," "approximately," and "substantially," are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

One skilled in the art will appreciate further features and advantages of the invention based on the above-described embodiments. Accordingly, the present application is not to be limited by what has been particularly shown and described, except as indicated by the appended claims. All publications and references cited herein are expressly incorporated by reference in their entirety.

What is claimed is:

1. A method comprising
receiving image data characterizing a viewed object, the image data acquired via an image sensor of a visual inspection system;
providing the image data via a display of the visual inspection system;
receiving a first directional movement input via a directional input device of the visual inspection system;
applying a first set of actuator drive signals to a plurality of actuators of the visual inspection system, causing the image sensor to move in a first real direction and causing points on the viewed object to move in a first visual direction on the display, wherein the first visual direction is in the direction of the first directional movement input;
applying, by a user, a coordinate transformation to the image data to generate transformed image data;
displaying the transformed image data on the display;
receiving a second directional movement input via the directional input device;
applying a second set of actuator drive signals to the plurality of actuators of the visual inspection system, causing the image sensor to move in the first real direction and causing points on the viewed object to move in a second visual direction on the display, wherein the second visual direction is in the direction of the second directional movement input.

2. The method of claim 1, wherein the coordinate transformation includes at least one of a horizontal mirroring transformation, a vertical mirroring transformation, or a rotation transformation.

3. The method of claim 1, wherein the visual inspection system is a video borescope.

4. The method of claim 1, wherein the image data and the transformed image data is provided for display during an inspection of industrial equipment using the visual inspection system.

5. The method of claim 1, wherein the coordinate transformation is applied via a manual gesture provided via the display or via a menu selection provided via the display.

6. The method of claim 1, further comprising providing a tip map graphic in the display, the tip map graphic including an indicator, wherein a position of the indicator within the tip map graphic corresponds to a direction and an amount of movement of the plurality of actuators, and further wherein the indicator moves in the first visual direction in response to the first directional movement input and moves in second visual direction in response to the second directional input movement.

7. The method of claim 1, wherein the plurality of actuators are articulated via pneumatic, hydraulic, memory metal, or direct drive articulation mechanisms.

8. A borescope system comprising
an image sensor, a display, a plurality of actuators mechanically coupled to the image sensor, a directional input device, a processor, and a memory storing computer-readable executable instructions, wherein the plurality of actuators move the image sensor based on received actuator drive signals and the processor is configured to execute the instructions causing the processor to perform operations including
receiving image data characterizing a viewed object acquired via the image sensor;
providing the image data via the display;
receiving a first directional movement input via the directional input device;
applying a first set of actuator drive signals to the plurality of actuators, causing the image sensor to move in a first real direction and causing points on the viewed object to move in a first visual direction on the display, wherein the first visual direction is in the direction of the first directional movement input;
applying, by a user, a coordinate transformation to the image data to generate transformed image data;
displaying the transformed image data on the display;
receiving a second directional movement input via the directional input device; and
applying a second set of actuator drive signals to the plurality of actuators to, causing the image sensor to move in the first real direction and causing points on the viewed object to move in a second visual direction on the display, wherein the second visual direction is in the direction of the second directional movement input.

9. The borescope system of claim 8, wherein the coordinate transformation includes at least one of a horizontal mirroring transformation, a vertical mirroring transformation, or a rotation transformation.

10. The borescope system of claim 8, wherein the image data and the transformed image data is provided for display during an inspection of industrial equipment.

11. The borescope system of claim 8, wherein the borescope system includes a graphical user interface provided via the display.

12. The borescope system of claim 11, wherein the coordinate transformation is applied via a manual gesture provided via the display or via a menu selection provided via the graphical user interface.

13. The borescope system of claim 8, wherein the processor is further configured to provide a tip map graphic in the display, the tip map graphic including an indicator, wherein a position of the indicator within the tip map graphic corresponds to a direction and an amount of movement of the plurality of actuators, and further wherein the indicator moves in the first visual direction in response to the first directional movement input and moves in second visual direction in response to the second directional input movement.

14. The borescope system of claim 8, wherein the plurality of actuators are articulated via pneumatic, hydraulic, memory metal, or direct drive articulation mechanisms.

* * * * *